(12) United States Patent
Mertens et al.

(10) Patent No.: US 6,757,637 B2
(45) Date of Patent: Jun. 29, 2004

(54) METHOD FOR CHECKING THE CONTENT OF POCKETS IN A BLISTER PACKAGE

(75) Inventors: Richard Mertens, Laupheim (DE); Heino Prinz, Laupheim (DE)

(73) Assignee: Uhlmann VisioTec GmbH, Laupheim (DE)

( * ) Notice: Subject to any disclaimer, the term of this patent is extended or adjusted under 35 U.S.C. 154(b) by 135 days.

(21) Appl. No.: 09/965,416

(22) Filed: Sep. 27, 2001

(65) Prior Publication Data

US 2002/0077771 A1 Jun. 20, 2002

(30) Foreign Application Priority Data

Sep. 27, 2000 (EP) ............................................ 00 121 032

(51) Int. Cl.[7] ............................ G01B 11/28; G01F 17/00
(52) U.S. Cl. ........................................ 702/156; 73/149
(58) Field of Search ............................ 702/52, 55, 156, 702/81–84, 182; 73/149, 304 C; 700/281, 240; 222/64; 53/503

(56) References Cited

U.S. PATENT DOCUMENTS

| | | | |
|---|---|---|---|
| 2,142,920 A | 1/1939 | Rose ............................ 209/82 |
| 4,245,243 A | 1/1981 | Gutjahr et al. .............. 358/106 |
| 4,847,487 A | 7/1989 | Bordini ....................... 250/223 |
| 5,750,938 A | * 5/1998 | De Caris et al. .............. 177/50 |
| 5,880,364 A | * 3/1999 | Dam ............................ 73/149 |
| 6,270,726 B1 | * 8/2001 | Tyberg et al. ................ 422/100 |
| 2001/0052986 A1 | * 12/2001 | Nantel et al. ................ 356/625 |

FOREIGN PATENT DOCUMENTS

EP 0302727 2/1989 .......... G01N/27/24

* cited by examiner

*Primary Examiner*—Marc S. Hoff
*Assistant Examiner*—Manuel L. Barbee
(74) *Attorney, Agent, or Firm*—Wood, Herron & Evans, LLP

(57) ABSTRACT

The present invention relates to a method for checking the filling or content of pockets in a blister package in particular for pharmaceuticals which is filled with a powdery, solid, liquid or pasteous substance whereby the volume filled of the substance is detected by a sensor and the detected volume value is supplied to an evaluation unit in which a comparison of the detected volume value with a volume target value is carried out. The sensor can preferably be formed both as a line sensor as well as a matrix sensor.

5 Claims, 2 Drawing Sheets

METHOD FOR CHECKING THE CONTENT OF POCKETS IN A BLISTER PACKAGE

The present application claims priority to European Patent Application No. 00 121 032.7 filed Sep. 27, 2000, the disclosure of which is hereby incorporated herein by reference in its entirety.

BACKGROUND OF THE INVENTION

1. Field of the Invention

The present invention relates to a method for checking the filling or the content of compartments or pockets in a blister package in particular for pharmaceutical products.

2. Scope of the Prior Art

Powdery or solid pharmaceutical substances are packaged in pockets in blister packages and are obtained by the patient in such packages. Liquid and pasteous substances can also be packaged in pockets of blister packages. All such substances may comprise one compound or several compounds.

With pharmaceuticals, the highly precise filling per pocket of the desired quantity is crucial, something that has led to the creation of very elaborate control devices. Conventionally, the quantities are checked by weighing them.

A device for weighing pharmaceutical receptacles, particularly ampoules, is known from DE 199 20 494 A1 which shows a weighing device with weighing pockets for weighing the receptacles prior to and after they are filled. By means of a gripper the receptacles are removed during a resting phase of a rhythmically operating conveyor device in the vicinity of the filling facility and are weighed. Then, the receptacles are re-fed to the conveyor device for filling and after being filled are again removed and weighed. Even if the device is supposed to be relatively simple in structure, as indicated in this publication, and only requires very little space, still its main disadvantage lies in the fact that due to weighing the receptacles, e.g. the pockets, twice prior to and after they are filled, a considerable amount of time is needed for checking the filling.

Up to 120 pockets per second are filled on a high-performance blister machine developed for filling of solid and powdery pharmaceuticals. Due to this high quantity, control is carried out by weighing them on a random basis. In doing so, a sample is automatically drawn, that sample is fed to the scale by means of a handling system, the filled pocket is weighed, the pocket emptied, for instance by blowing out the powder, the empty pocket is weighed and the differential value is accordingly calculated.

The random sampling check is, however, not sufficient for ensuring correct filling of the pockets since with filling quantities below one milligram per pocket it is obvious that deviations of the most minute filling quantities mean incorrect filling.

SUMMARY OF THE INVENTION

The object of the present invention is to provide a method for checking the filling or content of pockets in a blister package in particular for pharmaceuticals, where the pockets were filled with a substance, with which process a very large number of the filled volumes can be checked and the checking occurs fast enough to enable the control of a filling which is performed with high-performance machinery.

The method according to the invention is provided for checking the filling or content of pockets of a blister package in particular for pharmaceuticals which is filled with a powdery, solid, liquid or pasteous substance. The volume of the substance is detected by a sensor and the detected volume value is supplied to an evaluation device in which a comparison of the detected volume value with a volume target value is carried out.

This ensures that the volume filled in the packages is detected and checked while avoiding an interruption of the filling process by a weighing process and avoiding a loss of the volume of pharmaceuticals in the random sampling process.

With direct detection of the filled volume, the time thus needed is extremely reduced when compared with the time needed for weighing as described above, allowing for a significant Increase in the filling quantity per unit of time.

In particular, detection of the filled volume occurs without any contact, which likewise contributes to a further saving of time in checking.

Preferably, the comparative value between the volume value detected and the volume target value is displayed by means of a display device. In this way, for instance, filling machine operating personnel can at any time check on the filled volume.

If, according to the invention, each pocket of the package is detected by means of a sensor, then there is a 100-percent check on the filled pharmaceuticals, which ensures the correct filling of all pharmaceuticals.

Preferably, the number of sensors provided should correspond to the number of pockets in a package row, in which way a so-called line sensor is created with which all pockets in a package row can be checked. Recording can thus take place both if the package is in motion as well as if it is at rest.

Alternatively, the number of sensors can correspond to the number of pockets of a package, i.e. filling is checked with a so-called matrix sensor. It is obvious that with simultaneous checking of several or many pockets a correspondingly rapid filling can be achieved.

For highly precise recording of the volume of the substance located in a pocket, detection is accomplished by means of a matrix sensor when the package is at rest. This resting phase is, however, extremely brief since the sensor is in a position to carry out recording in an extremely short period of time. As an example: for recording, only several microseconds are required.

It is particularly advantageous if the sensor used in the process is a capacitive test probe having a simple structure and providing a detection signal which can be processed in a simple manner and which preferably measures the induced dipol moment (the electrical polarization) in any given volume of any material by means of a high frequency alternating field.

Alternatively, the sensor can also be an optically three-dimensional image recording sensor with the aid of which the filling volume can be calculated exactly.

The substances to be checked can be powdery, solid, liquid or pasteous substances, in particular pharmaceuticals. Such substances may have one compound or several compounds.

Further details, features and advantages of the present invention emerge from the following description with reference made to the drawings.

DETAILED DESCRIPTION OF THE PREFERRED EMBODIMENT

Figure 1:
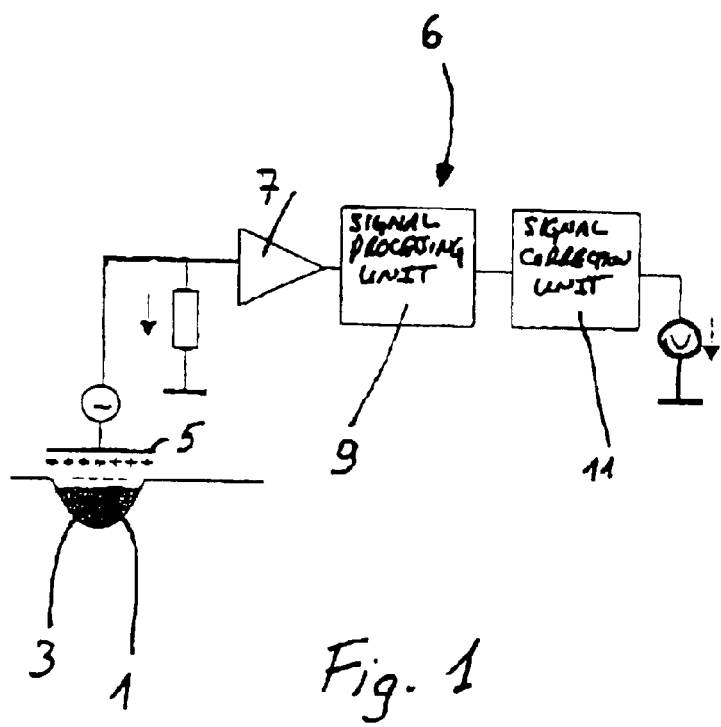
FIG. 1 shows a block diagram of an embodiment of the sensor and evaluation electronic system according to the Invention.

In FIG. 1 the sensor and evaluation electronic system is depicted in a block diagram with the aid of which the method according to the invention can be carried out. In a pocket 1 there is a powdery pharmaceutical 3 whose volume is to be checked. Pocket 1 is a pocket of a conventional and widespread blister package having several pockets which are normally arranged in rows.

By means of a sensor 5, the volume of the pharmaceutical 3 is detected without any contact. As is obvious from FIG. 1, sensor 5 is a capacitive test probe, which preferably measures the induced dipol moment (the electrical polarization) in any given volume of any material by means of a high frequency alternating field, generating a signal that via a pre-amplifier is supplied to a signal processing unit 9 and subsequently to a signal correction unit 11. The signal correction unit functions, for example, for zero line compensation. The pro-amplifier 7, the signal processing unit 9 and the signal correction unit 11 together form an evaluation unit 6.

The sensor 5, for instance, can be formed such that it only tests one pocket 1.

Figure 2:
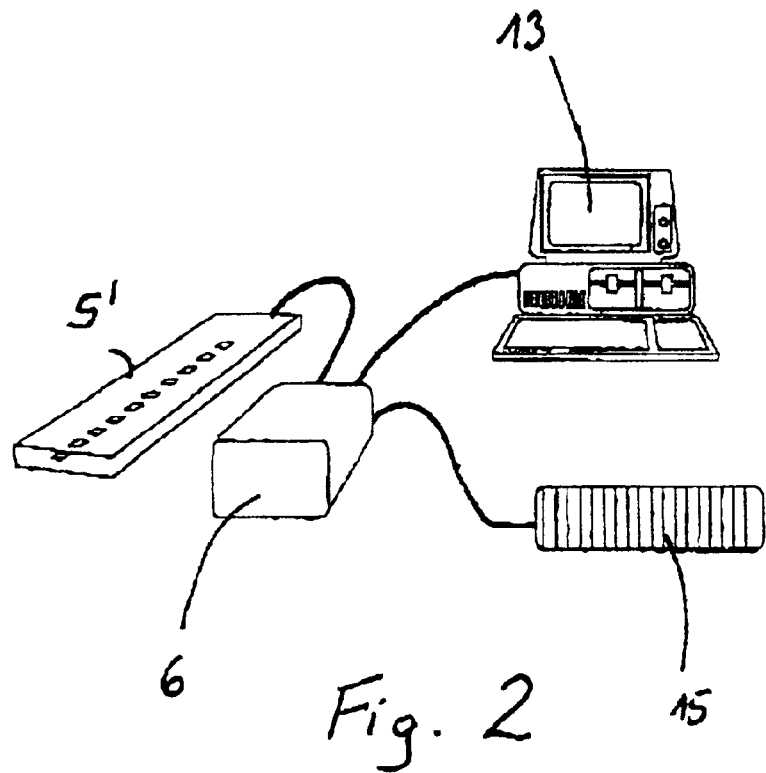
FIG. 2 shows an embodiment of the sensor system comprising a line sensor.

In FIG. 2, the preferred embodiment of the sensor as a line sensor 5' is depicted. This sensor is connected to the evaluation unit 6 comprising, for example, the pre-amplifier 7, the signal processing unit 9 and the signal correction unit 11. The evaluation unit 6 is according to FIG. 2 connected to a data processing unit, by way of example in the form of a PC 13, which is used for manipulation and for visualisation. Additionally, the evaluation unit is connected to the machinery controls or SPS 15 of the pharmaceutical filling device which accordingly controls and influences the filling of the packages with the pharmaceutical.

Figure 3:
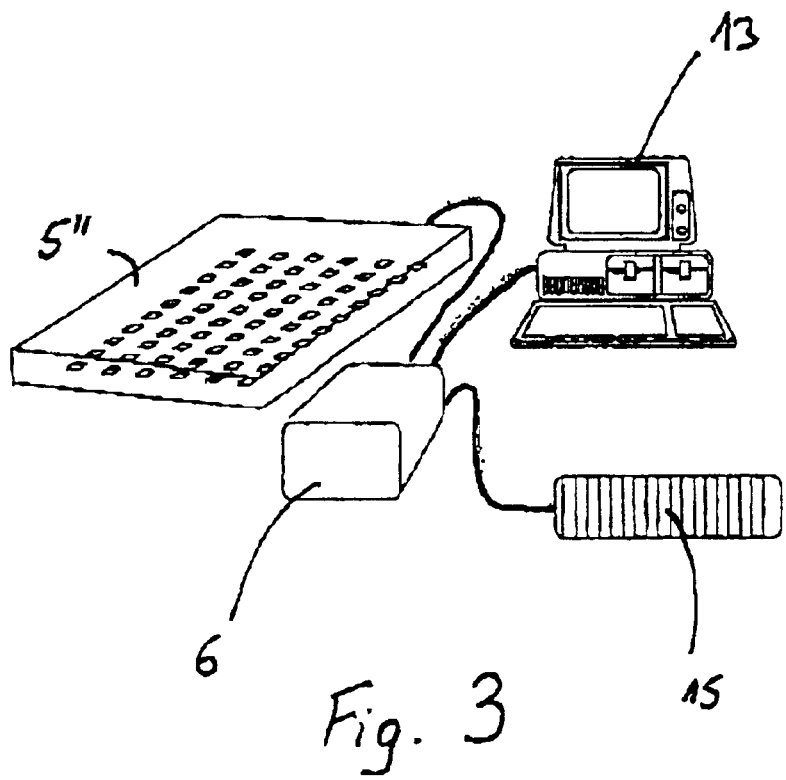
FIG. 3 shows an embodiment of a sensor system comprising a matrix sensor.

The embodiment according to FIG. 3 differs from that in FIG. 2 by the fact that instead of a line sensor 5' a matrix sensor 5" is connected with the evaluation unit 6. As can be seen from FIG. 3, the matrix sensor 5" has a large number of individual detection sensors whose arrangement corresponds to that of pockets 1 in the blister package. In this way, a large number of pockets 1 can be detected, for instance all volumes filled of one package or of several packages simultaneously, whereby corresponding high-performance filling is made possible with complete checking of all pockets filled, As known in the art, the blister packages are fed to a filling machinery and the pockets are filled with the respective substance. Then the method for checking the volume content of the pockets is carried out and subsequently the blister packages are dosed with a lid material as known in the art.

The sensor 5, 5', 5" comprises primary or real time electronics delivering a signal to a controller of the evaluation unit which compares the signal to any preset nominal value or target value, respectively. Via a signal interface the signal Is delivered to the subsequent machinery, for example the packaging machine of the filled blister packages. The controller device which incorporates the evaluation unit also stores and controls the sensor parameters.

When the detected volume value corresponds to the volume target value, the evaluation unit issues a "good"-signal for the further processing device and this device further operates the meanwhile closed blister packages. It is to be understood that with "target value" a range of volume values is meant and this range can be predetermined or preselected in the evaluation means.

When the detected volume value does not correspond to the target value or target value range, the evaluation unit issues a "non-good"-signal and the incorrect filled blister packaging is sorted out, The described method of the present invention is able to check the volume and all related properties which can be derived of the content of pockets of blister packages. This includes also the check whether a pocket is filled at all, i.e. non-filled pockets are detected as well.

What is claimed is:

1. A method for checking the content of pockets in a blister package which are filled with a powdery, solid, liquid or pasteous substance comprising the steps of:

detecting a filled volume of said substance in each of said pockets by a single measurement performed by a sensor formed as a capacitive test probe, which measures the induced dipol moment in any given volume of material by means of a high frequency alternating field;

supplying said detected volume value to an evaluation unit; and comparing said detected volume value with a volume target value by means of said evaluation unit.

2. A method according to claim 1 further comprising the step of displaying a comparison value derived from the comparison of said detected volume value with said volume target value by means of a display device.

3. A method according to claim 1 further comprising the step of detecting each pocket of the package by means of said sensor.

4. A method according to claim 3 wherein the number of the sensors provided for corresponds to the number of pockets in a row of the package.

5. A method according to claim 3 wherein the number of the sensors provided for corresponds to the number of pockets in a package.

* * * * *

UNITED STATES PATENT AND TRADEMARK OFFICE
CERTIFICATE OF CORRECTION

PATENT NO.      : 6,757,637 B2
DATED           : June 29, 2004
INVENTOR(S)     : Mertens et al.

It is certified that error appears in the above-identified patent and that said Letters Patent is hereby corrected as shown below:

Column 2,
Line 14, change "significant Increase in" to -- significant increase in --
Line 67, change "Invention;" to -- invention; --

Column 3,
Line 23, change "The pro-amplifier 7," to -- The pre-amplifier 7, --
Line 55, change "packages are dosed" to -- packages are closed --

Column 4,
Line 5, change "signal Is delivered" to -- signal is delivered --
Line 21, change "packaging is sorted out," to -- packaging is sorted out. --

Signed and Sealed this

Twenty-first Day of December, 2004

JON W. DUDAS
*Director of the United States Patent and Trademark Office*